(12) United States Patent
Kalvesten et al.

(10) Patent No.: US 9,936,918 B2
(45) Date of Patent: Apr. 10, 2018

(54) INSULATION OF MICRO STRUCTURES

(71) Applicants: Edvard Kalvesten, Hagersten (SE); Thorbjorn Ebefors, Huddinge (SE); Anders Eriksson, Sollentuna (SE)

(72) Inventors: Edvard Kalvesten, Hagersten (SE); Thorbjorn Ebefors, Huddinge (SE); Anders Eriksson, Sollentuna (SE)

(73) Assignee: SILEX MICROSYSTEMS AB, Jarfalla (SE)

( * ) Notice: Subject to any disclaimer, the term of this patent is extended or adjusted under 35 U.S.C. 154(b) by 864 days.

(21) Appl. No.: 14/367,053

(22) PCT Filed: Nov. 29, 2012

(86) PCT No.: PCT/SE2012/051325
§ 371 (c)(1),
(2) Date: Jun. 19, 2014

(87) PCT Pub. No.: WO2013/095260
PCT Pub. Date: Jun. 27, 2013

(65) Prior Publication Data
US 2014/0378804 A1    Dec. 25, 2014

(30) Foreign Application Priority Data
Dec. 22, 2011    (SE) ........................ 1151268

(51) Int. Cl.
*A61B 5/04*    (2006.01)
*H01L 21/02*   (2006.01)
(Continued)

(52) U.S. Cl.
CPC .......... *A61B 5/685* (2013.01); *A61B 5/04001* (2013.01); *A61M 37/0015* (2013.01);
(Continued)

(58) Field of Classification Search
CPC ..... A61B 5/0478; A61B 5/0492; A61B 5/685; A61B 5/6868; A61B 5/04001; G01R 3/00;
(Continued)

(56) References Cited

U.S. PATENT DOCUMENTS

| 5,747,839 A | 5/1998 | Hammond et al. |
| 7,560,802 B2 | 7/2009 | Kalvesten et al. |
| 2003/0045124 A1 | 3/2003 | Shih et al. |

FOREIGN PATENT DOCUMENTS

| DE | 10129846 | 11/2002 |
| WO | 2004084300 | 9/2004 |

(Continued)

OTHER PUBLICATIONS

International Search Report dated Apr. 2, 2013, corresponding to PCT/SE2012/051325.

*Primary Examiner* — Lee S Cohen
*Assistant Examiner* — Eunhwa Kim
(74) *Attorney, Agent, or Firm* — Young & Thompson

(57) ABSTRACT

A method of providing a metal coating on a substrate (10), and electrically insulating sections/parts of the metal coated substrate from each other. A substrate is provided with an insulating material in the substrate, the insulating first material extending through the thickness of the substrate and protruding above one surface of the substrate. It forms an enclosed section/portion (14) of the substrate. A protective structure (15) is provided on the insulating material such that it covers the entire circumference thereof. The insulating material is selectively etched to create an under-etch (18) under the protective structure. Finally conductive material (19) is deposited to provide a metal coating over the substrate, whereby the under-etch will provide a disruption in (Continued)

the deposited metal coating, thereby electrically insulating the enclosed section from the surrounding substrate.

10 Claims, 19 Drawing Sheets

(51) Int. Cl.
*H01L 21/762* (2006.01)
*A61B 5/00* (2006.01)
*A61M 37/00* (2006.01)
*H01L 21/768* (2006.01)
*H01L 23/48* (2006.01)
*H01L 21/308* (2006.01)
*G01R 1/067* (2006.01)
*G01R 3/00* (2006.01)

(52) U.S. Cl.
CPC .......... *H01L 21/02* (2013.01); *H01L 21/0226* (2013.01); *H01L 21/02334* (2013.01); *H01L 21/02362* (2013.01); *H01L 21/308* (2013.01); *H01L 21/762* (2013.01); *H01L 21/76224* (2013.01); *H01L 21/76229* (2013.01); *H01L 21/76898* (2013.01); *H01L 23/481* (2013.01); *A61M 2037/0053* (2013.01); *G01R 1/06744* (2013.01); *G01R 3/00* (2013.01); *H01L 2924/0002* (2013.01)

(58) Field of Classification Search
CPC .... G01R 1/06744; G01R 31/00; G01R 31/02; G01R 31/26; G01R 31/2601; G01R 31/2889; H01L 21/283; H01L 21/308; H01L 21/6224; H01L 21/02362; H01L 21/02234; H01L 21/0226; H01L 21/28123; H01L 21/28141; H01L 21/2815; H01L 21/76898; H01L 21/76224; H01L 21/76229; H01L 2924/0002; H01L 22/14; H01L 21/02; H01L 21/762; H05K 1/181; H05K 2201/07; A61M 2037/0053
USPC ......................................................... 438/424
See application file for complete search history.

(56) References Cited

FOREIGN PATENT DOCUMENTS

| WO | 2007070004 | 6/2007 |
| WO | 2008003564 | 1/2008 |

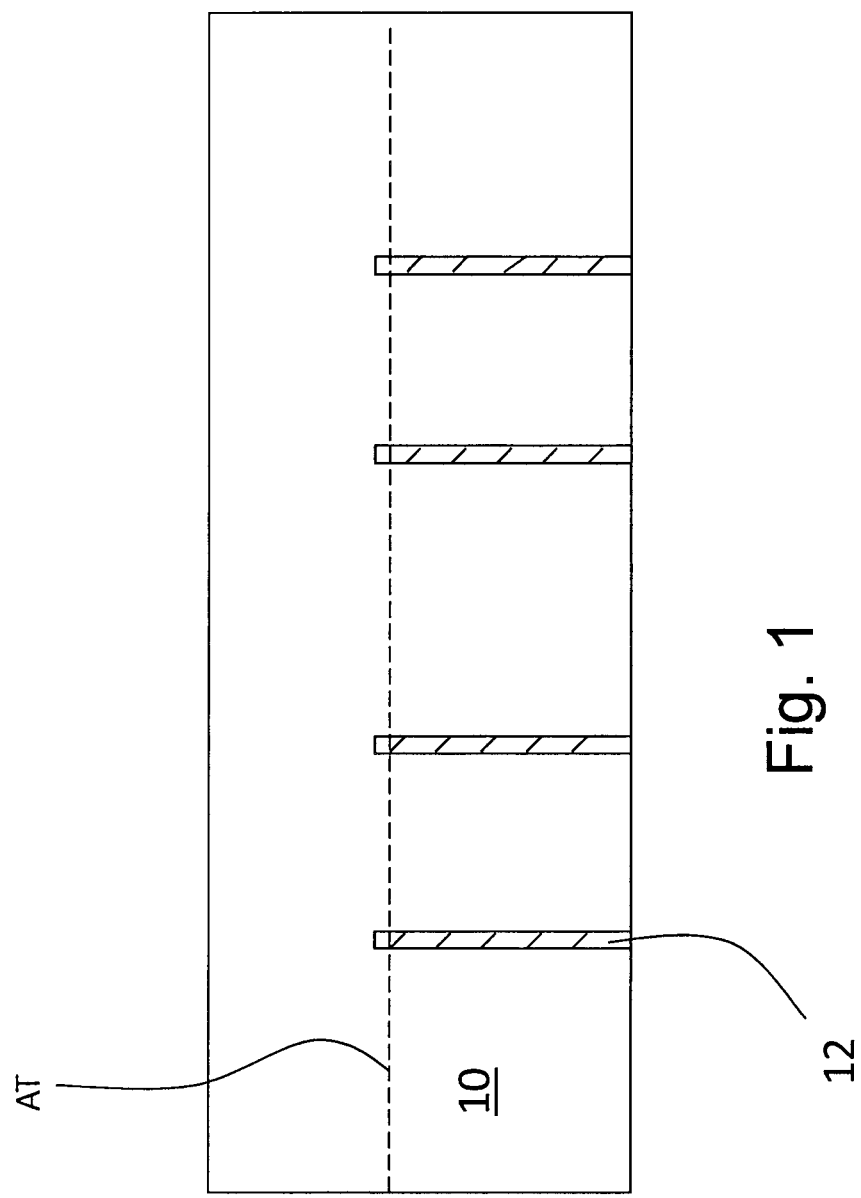

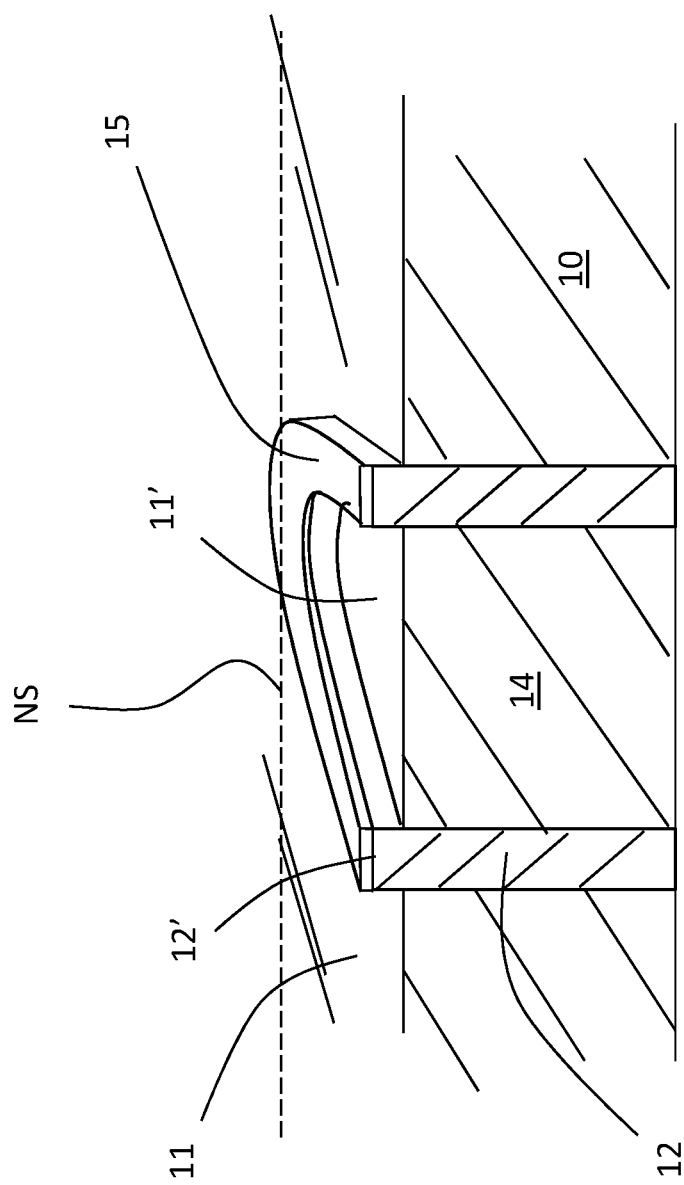

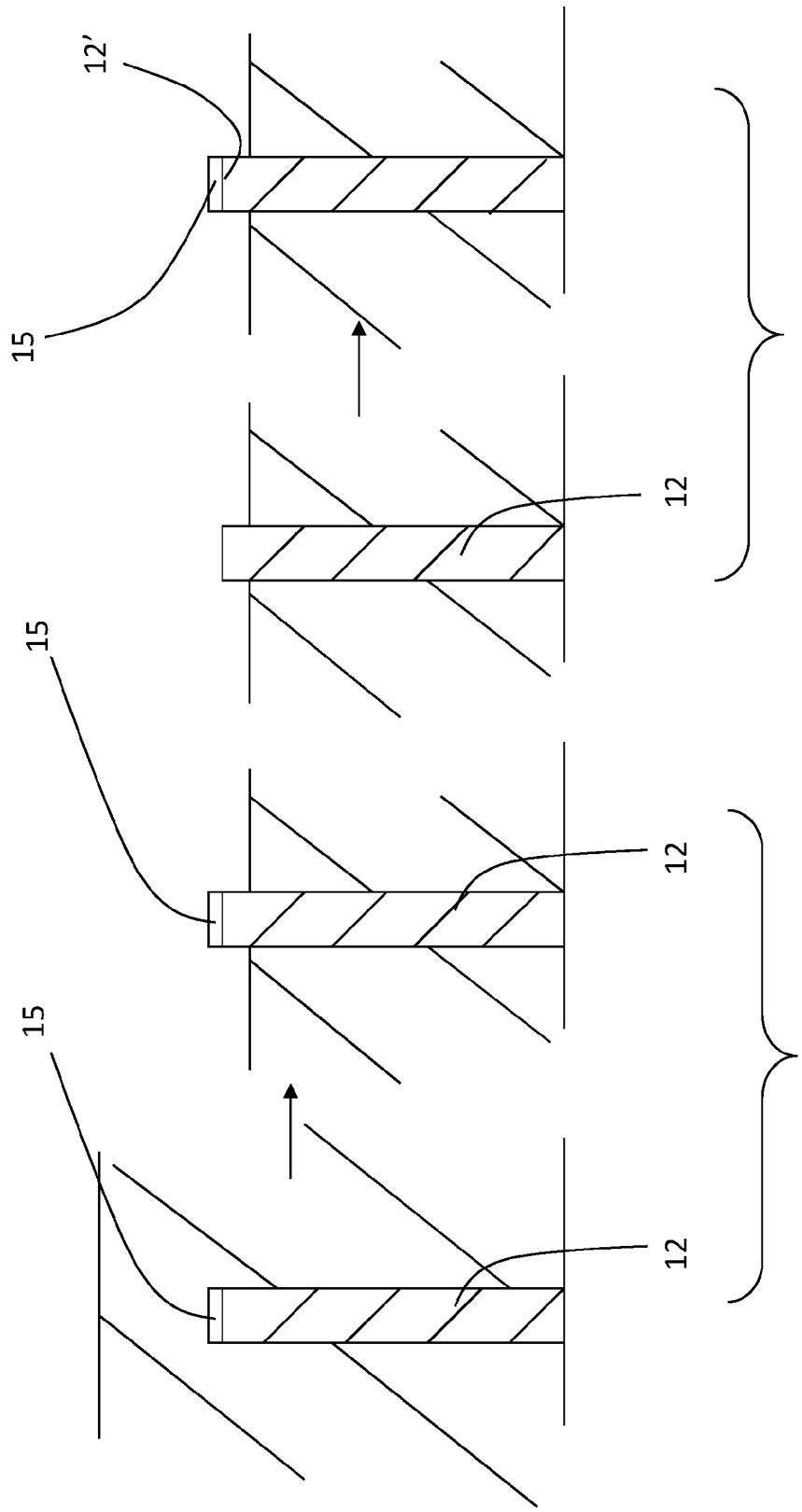

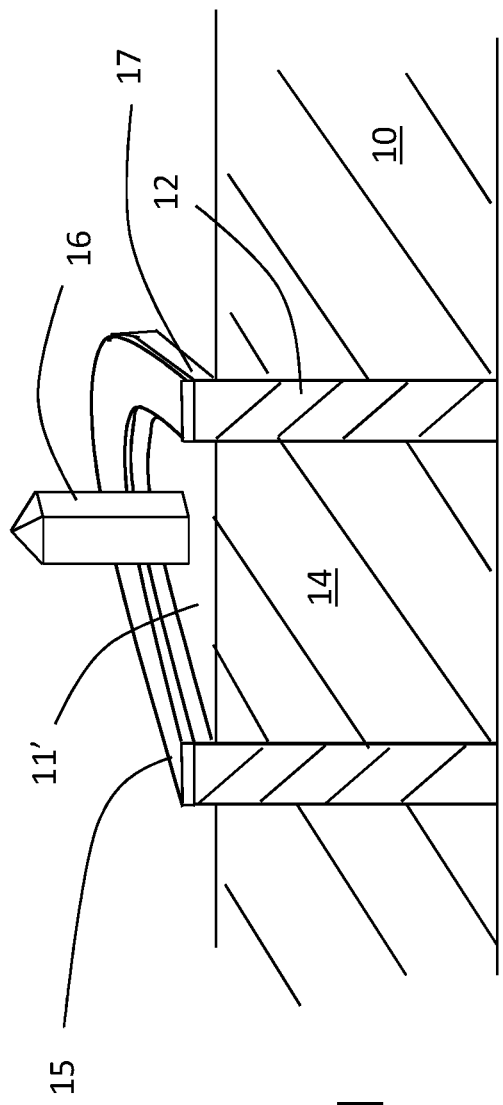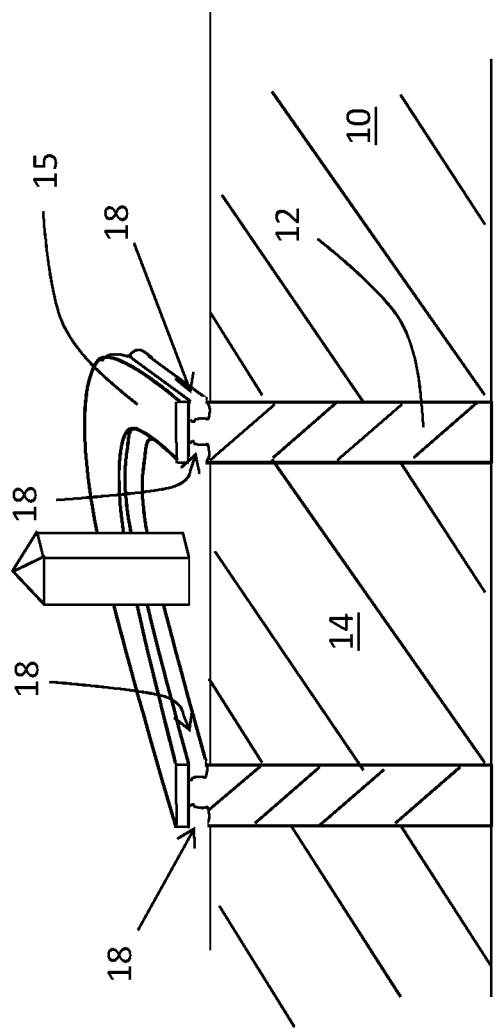

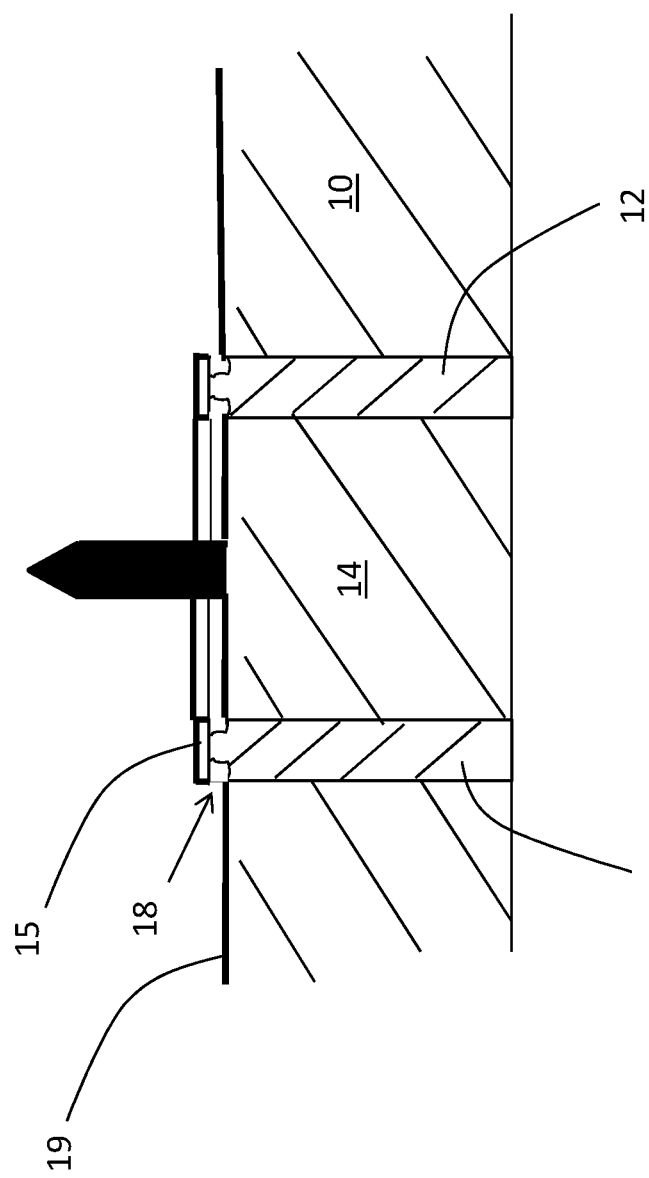

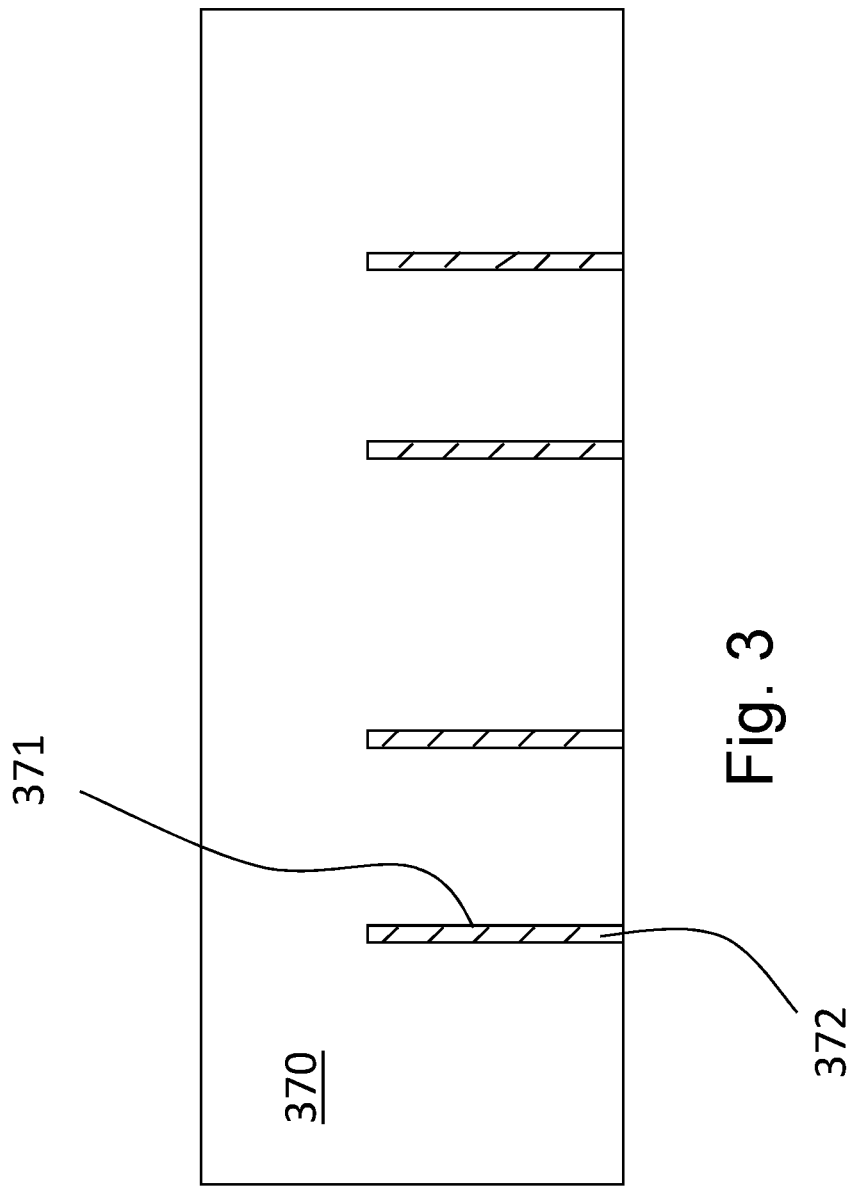

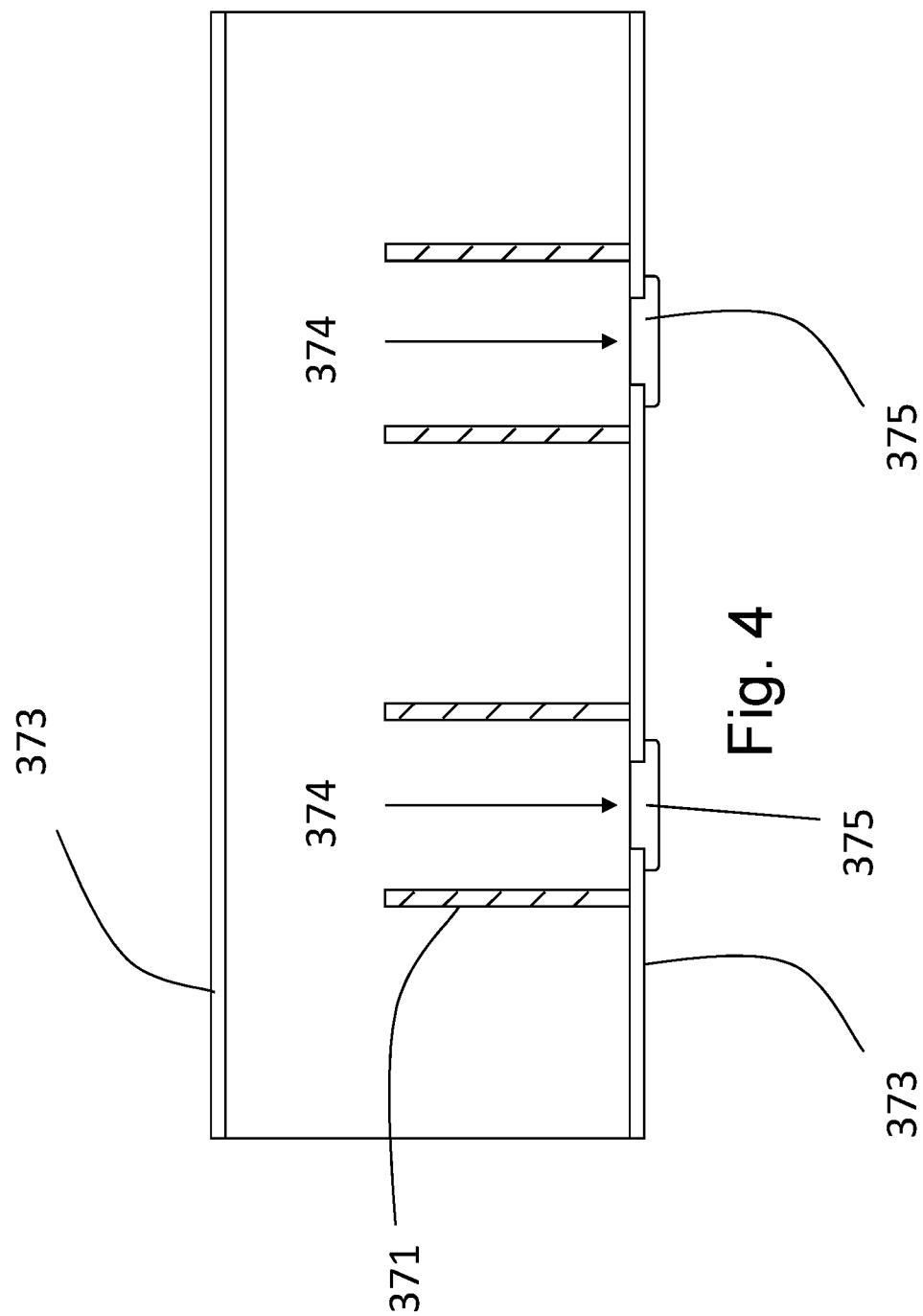

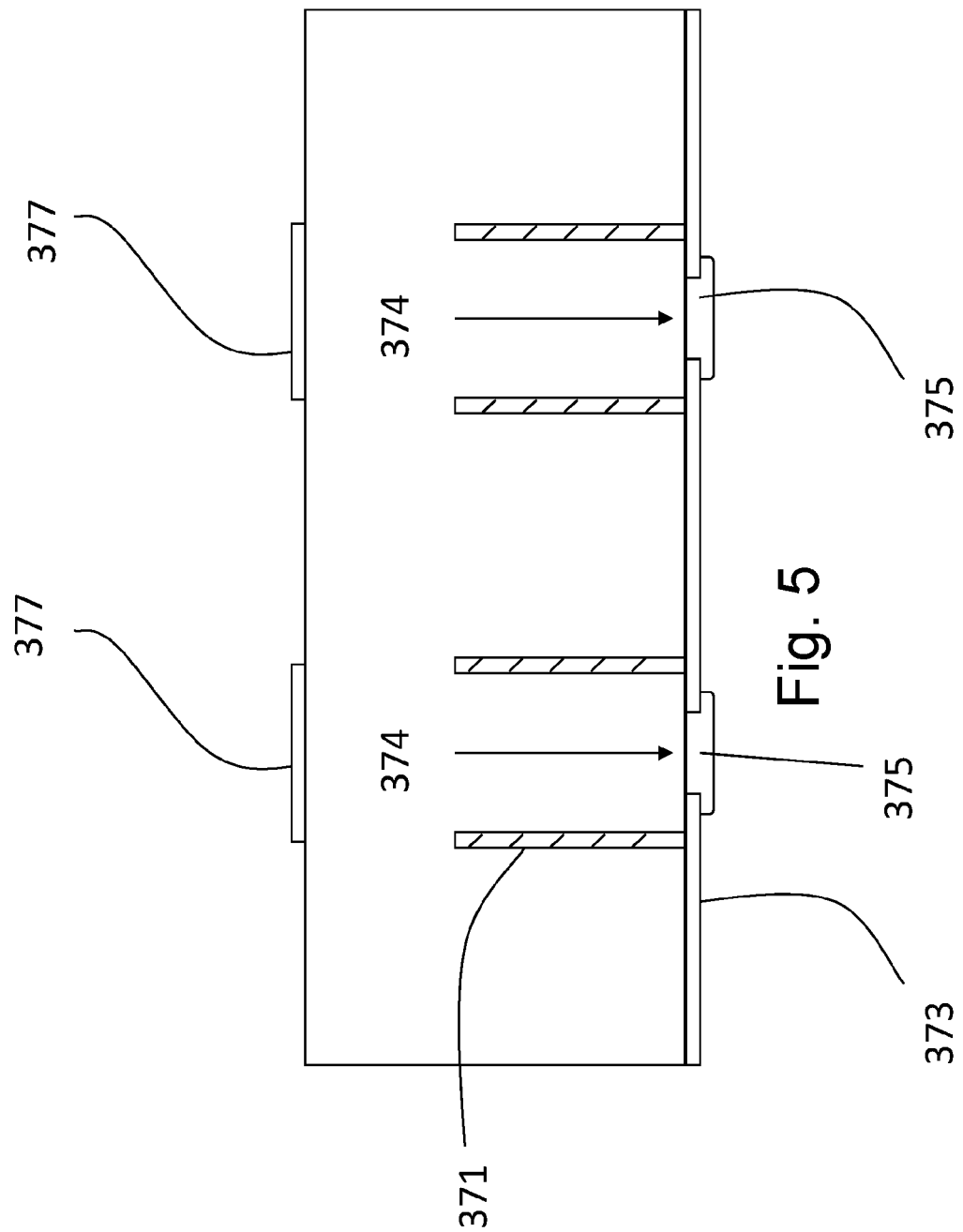

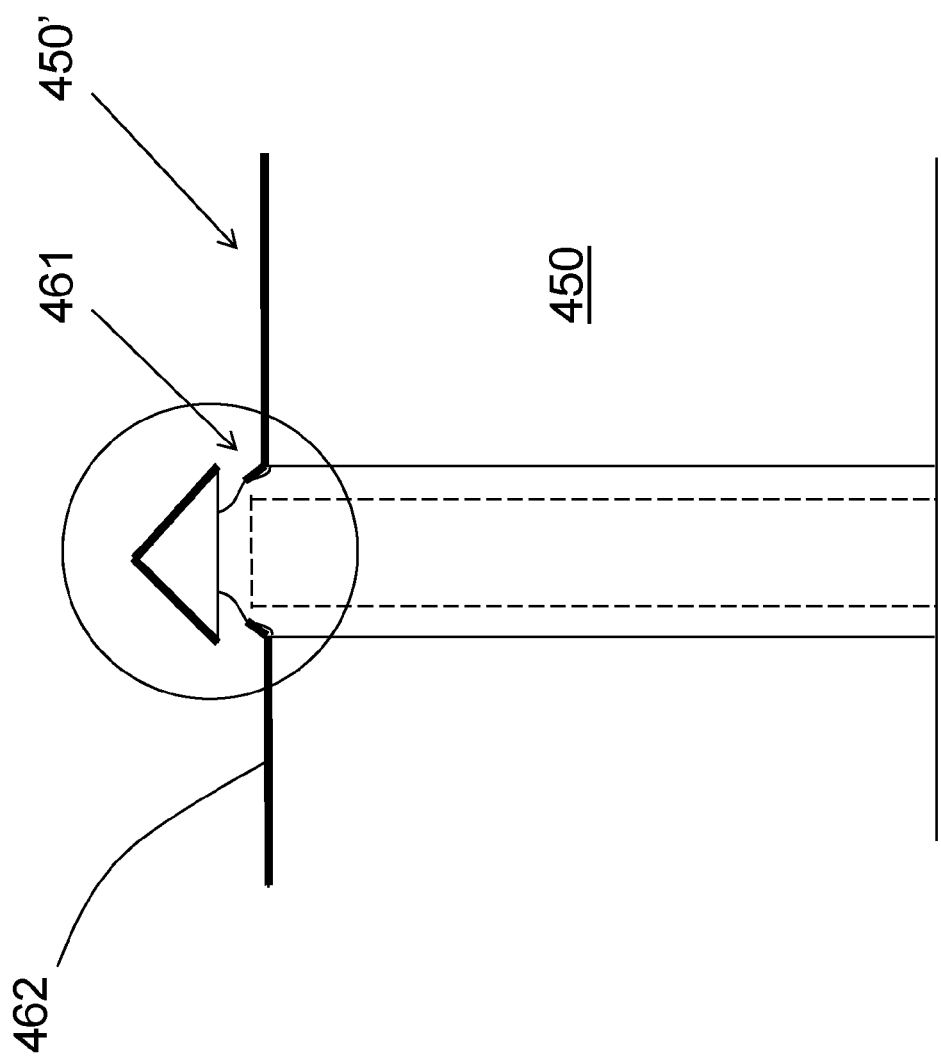

INSULATION OF MICRO STRUCTURES

The present invention relates to electrical insulation of groups of micro elements or individual micro elements on a substrate surface while maintaining electrical contact through said substrate. In particular it relates to making needles in the micrometer scale and to insulate these needles from each other laterally and still enabling signals picked up by such needles to be recorded from the backside of the substrate on which the needles are provided.

BACKGROUND

Micro-sized needles, i.e. needles having diameters and lengths in the micrometer range, find great utility i.a. in many medical applications.

Typical fields of application are various electrical measurements performed on the skin, using arrays of micro-needles. For electrical applications it is often desirable to provide individual needles or groups of needles that are electrically insulated from each other in the lateral direction, but where the needles are in electrical contact with the back-side of the substrate on which they are provided.

Other fields of application are for thin film thickness/impedance measurements (e.g. in the IC industry) where micro probe heads are needed. Also for chip probing robust miniaturized needles are required.

Such lateral insulation and vertical electrical "through connection" finds wider applications, and can be used for a plurality of applications where signals needed to be routed from a device through a substrate.

In U.S. Pat. No. 4,356,056 there is discloses a method using under-etching for the provision of mesa structures on a circuit-board.

SUMMARY

The present invention solves the problem of providing lateral insulation between different areas on a substrate, optionally having groups of elements, such as micro needles provided on the substrate surface, while allowing electrical signals to be routed through the substrate and picked up on the opposite side surface of the substrate, wherein the elements and the substrate have a conductive coating.

Thus, in the first aspect the invention provides methods for insulation in a lateral direction between surfaces areas on which elements or groups of elements can be provided on a substrate, and for providing electrical contact through the substrate, from the backside to the frontside, within each insulated area.

In a preferred embodiment of the first aspect there is provided a method for lateral electrical insulation of needles, while maintaining electrical contact through the substrate on which the needles are provided.

The method in its most general aspect is defined in claim 1.

In a second aspect there is provided a semiconductor device having laterally insulated micro elements on a first side surface of a substrate, electrically connected to the opposite side surface of the substrate.

In a further aspect the needles are coated with various metals selected to avoid thermo EMKs etc.

An advantage with the present method is that it is possible to provide insulation without the need of lithography and etching processes, since the existing structures in the substrate in fact is used for masking purposes during coating with metal. This leads to cost reduction in the manufacturing flow.

The present method also solves the issues related to patterning metal films without lithography and etching means, on semiconductor substrates having high aspect ratio of the topography on the surface.

The new methods and devices will now be described with reference to the appended drawings.

BRIEF DESCRIPTION OF THE DRAWINGS

FIG. 1 schematically illustrates the process of making a via structure;

FIG. 2a-f illustrates a process schematically;

FIG. 3 shows a first stage in a process for insulating a needle;

FIG. 4 shows a second stage in a process for insulating a needle;

FIG. 5 shows a third stage in a process for insulating a needle;

FIG. 16 shows an underetched insulating ridge in a finished stage.

DETAILED DESCRIPTION

Figure 6:
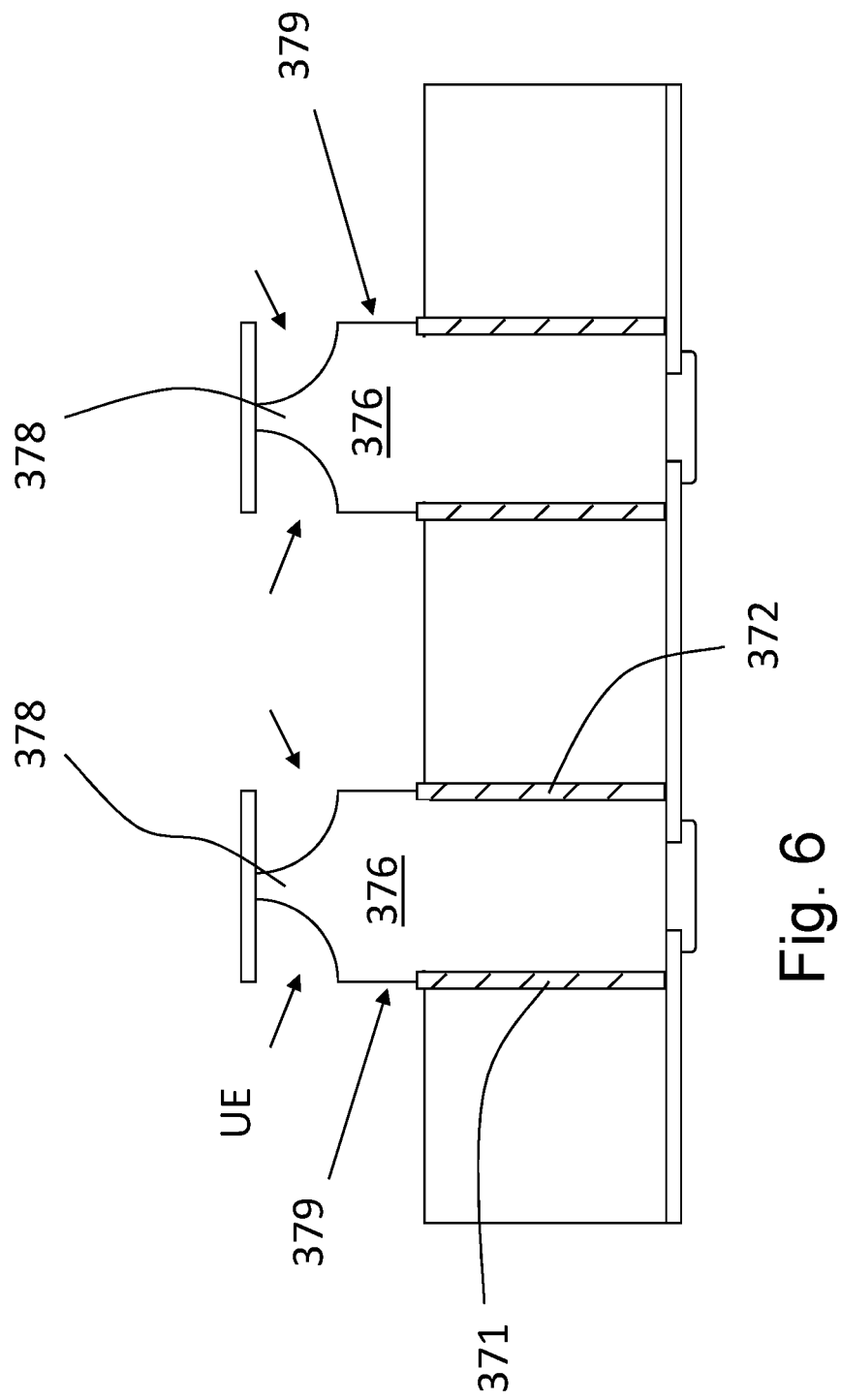
FIG. 6 shows a fourth stage in a process for insulating a needle.

All embodiments shown can be repeating units over an entire wafer.

The present invention in its most general aspect relates to metallizing a substrate, optionally having topology (i.e. the substrate is not flat and has any kind of component on it that extends upwards form the substrate surface) and the provision of a disruption in the metal coating, with insulating material provided in the gap between the portions of the metal coating in order to provide insulation of elements provided on one part of a substrate from the remainder of the substrate. Furthermore, the insulated portions are not only insulated laterally across the surface, but there is also insulation extending through the thickness of the substrate enclosing a piece of the substrate such that there is an electrical connection through the substrate which is not in electrical contact with the surrounding material in the substrate, whereby elements provided on the surface of a piece of the substrate enclosed accordingly, are electrically insulated in a lateral direction, but in electrical contact with the opposite side of the substrate from where they are provided. This kind of structure is commonly referred to as a "via" structure. In this particular case the via can consist of "wafer native material", i.e. the via is not made by filling a hole with a material.

The process of making a via is not part of the present invention per se, but is the subject of applicants own WO 2004/084300, and reference is made to that document for details relating to the actual making of vias and in particular vias on which there are provided needles. Herein only a very brief description will be given for ease of understanding of the disclosure below.

Thus, a substrate, such as a semiconductor wafer is provided. A trench is etched in the substrate from one side of the substrate 10 and extending almost through the substrate. The trench should form a closed loop in order to enclose a piece of the substrate. The trench is filled with insulating material 12, and then it is thinned down from the opposite side from which the trench was made. The thinning is performed to such an extent, and selectively, that only substrate material is removed, and deep enough that the insulating material becomes exposed, and also slightly further in order that the insulating material will protrude slightly from the substrate surface. This process is schematically illustrated in FIG. 1 wherein the surface after thinning is shown in a broken line AT. In FIG. 2a the structure after thinning is shown and the nominal surface of the substrate 10 is shown with a broken line NS, and it is clearly shown that the insulating material 12 in the trench extends up above the surface 11.

According to an embodiment there is provided a method for electrically insulating individual needles from each other while maintaining electrical contact through the substrate.

Thus, in FIG. 2a there is shown a cross-section through a substrate 10 having an insulating structure 12 provided in the substrate, extending through the thickness of the substrate 10 and extending above the substrate surface 11, such that it has an upper horizontal surface 12'. The insulating structure forms an enclosure electrically insulating a portion of the substrate from surrounding parts of the substrate. This enclosed and insulated structure is referred to as a "via" 14. Suitably the insulating material in the structure 12 is silicon oxide, or other well known insulating materials used in IC manufacturing. Normally the substrate is made from a semiconductor, and if it is suitably doped, the conductivity may be high enough to render it electrically conductive, i.e. having a resistitivty of <0.002 Ωcm.

Thereby the via 14 will be conductive, but at the same time electrically insulated from the surrounding substrate. Thus, a component of some kind arranged on the surface 11' of the via can provide signals or be actuated as the case may be by passing electrical current through the via or by applying a voltage across the substrate in the via.

In a case where it is desirable to provide a metal coating (or metallization) over the entire substrate, but still provide insulation of the enclosed area 11' from the surrounding metallized surface 11, the method according to the invention is used.

Thus, according to the invention, a protective layer 15 of a suitable material is provided on the horizontal surface 12' of the insulating material 12. This protective layer 15 can be provided in several different ways.

Either it can be achieved by appropriate masking of the substrate such that when the substrate is thinned down, there will be some material left on the top surface 12'. This alternative is described in more detail in connection with FIGS. 11-16.

Alternatively, it is also within the inventive concept to provide the required protective material 15 in the bottom of the trench before filling the trench with e.g. oxide 12, and before the substrate is thinned down. This is schematically shown in FIG. 2b.

Also, the protective layer 15 can be grown or deposited on the surface 12' of the trench by a suitable method, in which case the remainder of the substrate will have to protected by a mask. This is schematically shown in FIG. 2c.

Thus, as can be seen in FIG. 2a the insulating structure 12 will be coated on the top surface 12' to provide a protective top layer 15 on the insulating structure 12.

In a case where it is desired to attach a component to the via this can be done as shown in FIG. 2d, where a component 16 has been provided on the via surface 11'. Alternatively, there can be provided other structures such as needles in a previous step, possibly in the process sequence for providing the via structure. This will be described in further detail in connection with specific embodiments. However, for the purpose of the invention, it is not important whether or not there is a component provided on the via surface at all, or when it was made.

Thus, starting with the structure shown in FIG. 2d (with or without a component 16 provided on the via surface 11'), a selective etch (isotropic wet etch or isotropic dry etch), is applied to that part 17 of the oxide of the insulating structure 12 that extends above the substrate surface and the protective layer 15. The etch (for example wet HF) will excavate material from underneath the top protective layer 15' on the insulating structure and will thereby provide an under-etch 18 under the protective layer 15 on both sides of the protruding insulating structure 12, as can be seen in FIG. 2e.

When the under-etch is deep enough, metal is deposited over the substrate with a metal deposition process such as evaporation and sputtering. A coating 19 is thereby provided over the substrate, as illustrated in FIG. 2f. But, by virtue of the method described forming an under-etch, the excavated part forming the under-etch 18 will be "shadowed" by the top protective layer 15 of the insulating structure 12, and thus there will be a disruption in the metal coating 19 along the under-etch 18 in the insulating structure 12.

This renders the via electrically insulated from the rest of the wafer despite the metallization.

According to an embodiment there is provided a method for electrically insulating individual needles from each other while maintaining electrical contact through the substrate.

This particular embodiment of the method will now be described with reference to drawing FIGS. 3-10.

Thus, the process begins with providing a substrate semiconductor wafer 370 suitably made of silicon. In this wafer, as shown in FIG. 3, there are trenches 371 made defining an area on the wafer, i.e. an area encircled by a trench in a closed loop. Suitably this loop is circular or shaped as a torus, but it could take any shape suitable for the purpose at hand.

In the embodiment shown it is assumed that a circular trench is provided. The trench is made by standard lithographic methods involving making a mask, preferably by spinning on a resist, and opening up the resist where the trenches are to be made. Preferably the trenches are made by DRIE (Deep Reactive Ion Etch), suitably in a two step procedure described in e.g. U.S. Pat. No. 7,560,802 (Kälvesten et al). This is to avoid causing voids during subsequent filling of the trenches. The trenches are made to a depth such that enough wafer material is left unpenetrated by the etch that needles subsequently can be made from the other side.

The wafer is subjected to oxidation to cover it including the inner walls of the trenches with a thin oxide layer (not shown). If possible the entire trench is filled with oxide 372. Optionally the trenches are filled with some other suitable insulating material.

The structure thus obtained is a precursor structure for a final via (also referred to as a wafer-through connection) on which a needle is to be made.

Next, referring to FIG. 4, electrical contacts are made to the silicon within the area surrounded by the trenches, i.e. the via. To this end the wafer is oxidized/coated (grown or deposited) with insulating material, by methods well known to the skilled man, to provide for example an oxide layer 373 covering both sides of the wafer. On the trench side the oxide is patterned and etched so as to open up the oxide/TEOS layer over the vias, thereby forming exposed areas 374 on the via. A suitable metal alloy (for example Ti/Pt/Au) is deposited in the openings onto the silicon to provide contacts 375.

Now the needles 376 are made, reference is made to FIGS. 5-10. Needle manufacture is described in detail in co-pending WO 2007/070004. Thereby the oxide on the opposite side with respect to the contacts 375 described above, is patterned and subjected to an oxide etch to remove oxide from the surface such that a mask 377 defining the needles is left, shown in FIG. 5. Thereafter the needles are made by first performing an isotropic underetch UE under the mask 377 (as illustrated by the arrows) whereby the tips 378 of the needles 376 are created, as shown in FIG. 6. The etch method can be $SF_6$ gas process. Then an anisotropic etch (DRIE; switched etching/passivation process with gas mixture $SF_6$ and $C_4F_8$, respectively) is performed to create the vertical pillars 379 of the needles. This is the so called Bosch process. The latter etch is performed to a depth where the oxide 372 in the trenches 371 is exposed, shown in the encircled area in FIG. 7. The encircled area is shown magnified in FIG. 8.

Other methods to fabricate needles are presented in the above mentioned WO 2007/070004.

Figure 7:
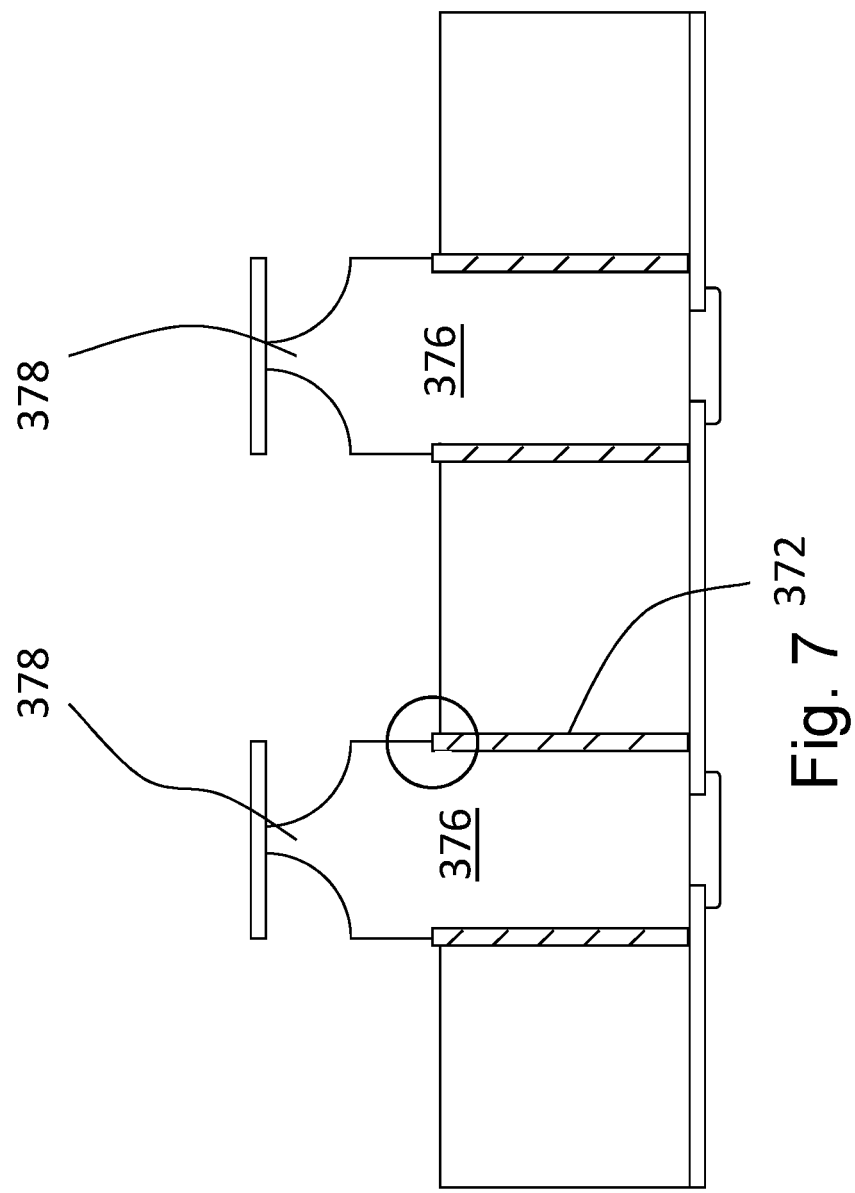
FIG. 7 shows a fifth in a process for insulating a needle.
Figure 8:
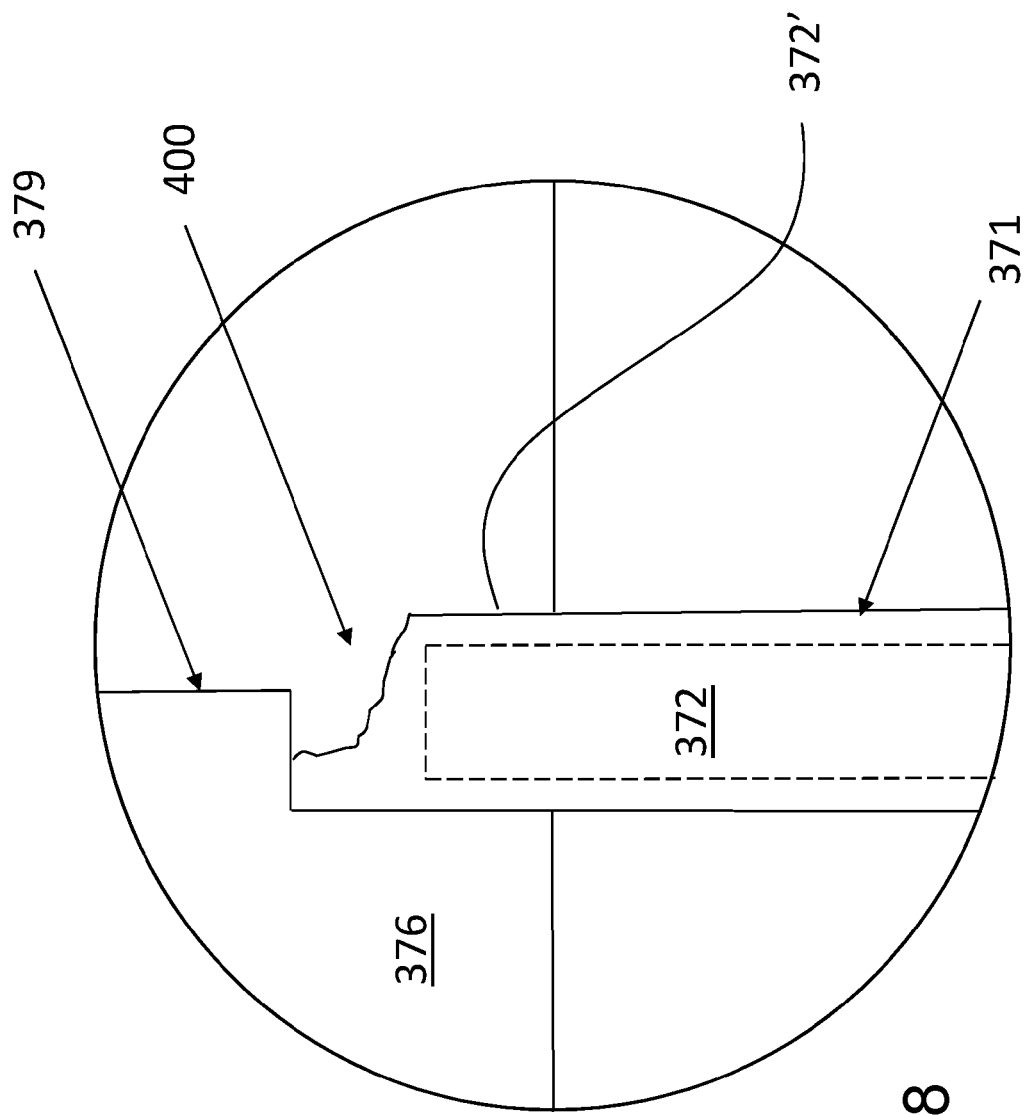
FIG. 8 is a close up of the encircled portion in FIG. 7.

A wet oxide etch is performed on the structure shown in FIG. 7 whereby the exposed oxide 372' in the trenches is selectively etched to form an undercut 400 in the material at the bottom end of the needle pillars 379, shown in FIG. 8.

It should be mentioned that other materials than oxide is possible, and other etches than HF is also possible.

Thus, it is important to align the mask elements 377 defining the location of the needles 376 very precisely such that the oxide in the trenches becomes accessible for the oxide etch.

Figure 9:
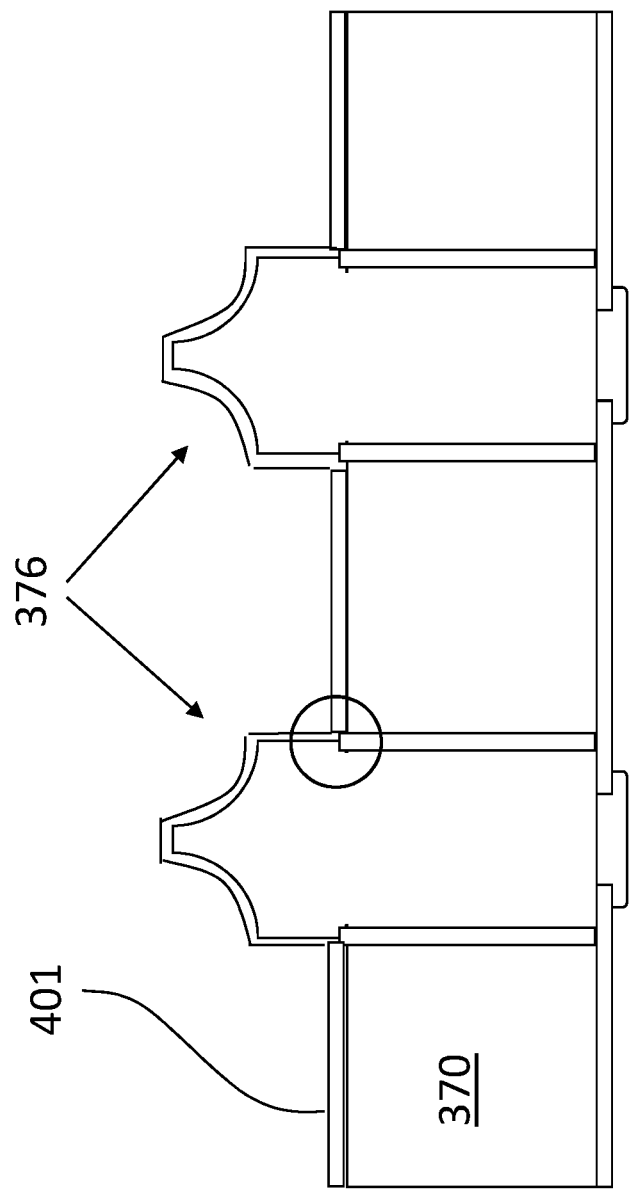
FIG. 9 shows a sixth third stage in a process for insulating a needle.
Figure 10:
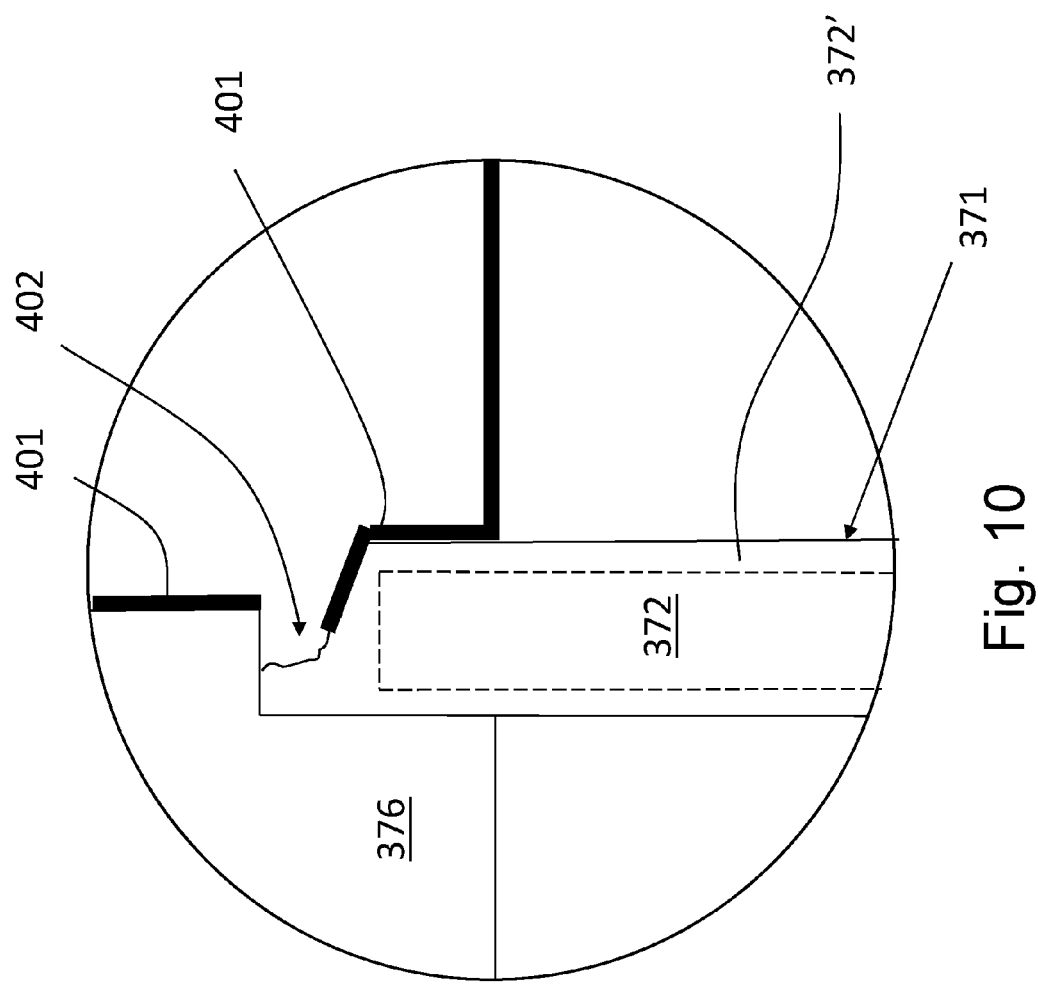
FIG. 10 is a close up of the encircled portion in FIG. 9.

In the next step the needles 376 and the entire wafer on the side carrying the needles are provided with a coating 401 by depositing a conductive material, suitably by evaporation or sputtering materials, such as Ag, AgCl, Au, Pt, Ru, suitable for the application in mind. FIG. 9 schematically illustrates a coated wafer 370 and needles 376. By virtue of the undercut provided by the wet oxide etch there will be a region that will not be accessible to the sputtered material and thus there will be a disruption in the conductive coating 401 along the periphery of the needle at its base. This is the encircled region in FIG. 9. This region is magnified in FIG. 10 wherein it is clearly seen that there is a disruption 402 in the coating 401.

Figure 15:
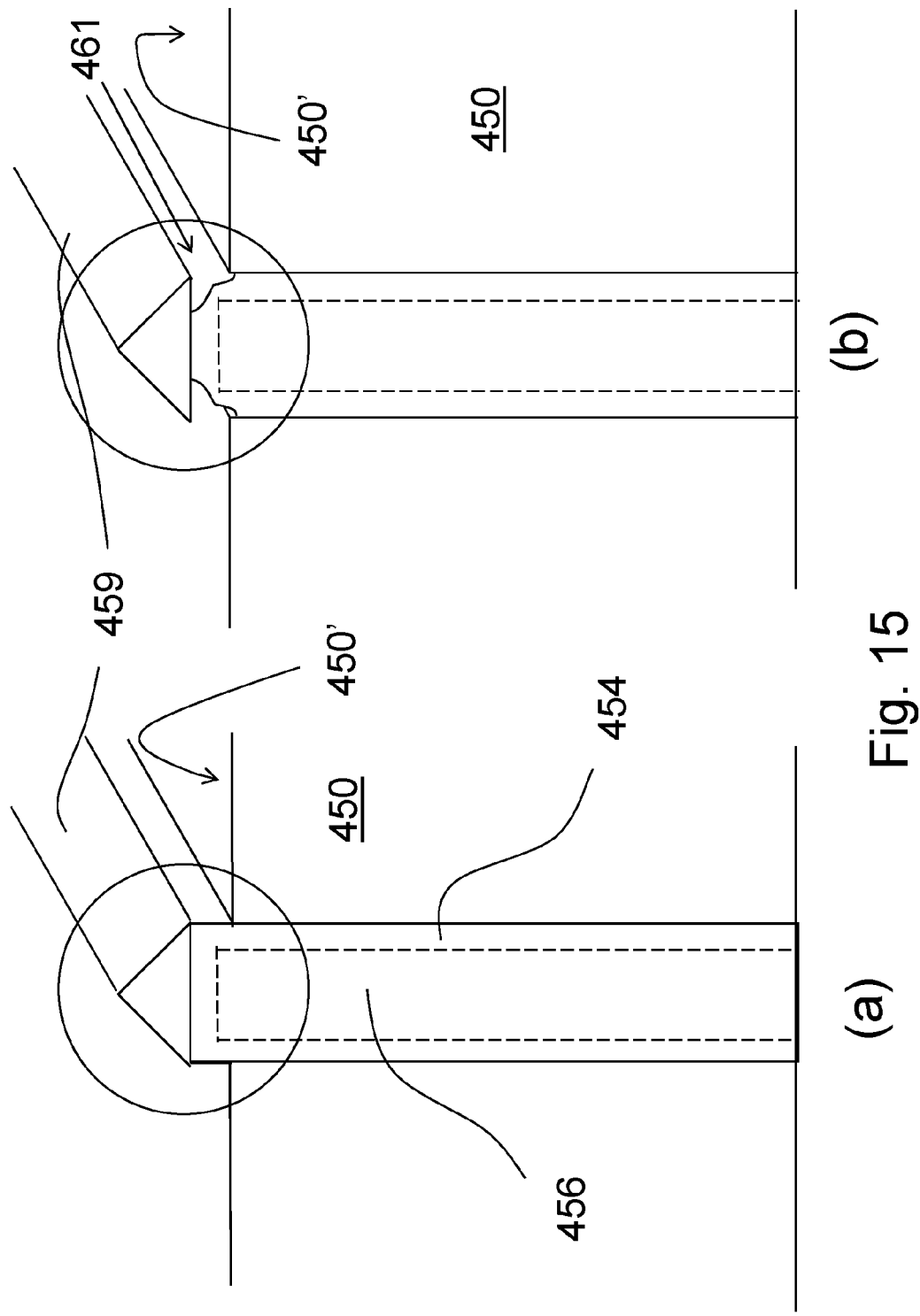
FIG. 15a shows an insulating ridge before underetch.
FIG. 15b shows an underetched ridge.

The dimensions of the underetch, i.e. how deep in under the protective material, i.e. the structure designated 15 in FIG. 2a-f or 379 in FIG. 8 or 459 in FIG. 15, or the width in vertical direction of the underetch, is above all dependent on how thick the metal coating to be applied will be. The thicker said metal coating is the wider and deeper the underetch needs to be. It should also be considered that the metal deposition processes (sputtering or evaporation) will not just coat in the vertical direction, and thus at least some metal will extend in under the protective layer. However, at least the "roof" of the underetch will not become coated, thereby ascertaining the required disruption in the metal coating.

In a still further embodiment there is provided a method of insulating groups of needles using the same principal approach as in the previous embodiment, i.e. to use an underetch to create an undercut portion which leaves a gap after subsequent metallization. The metal being deposited simply cannot become deposited on the undercut portion, since it is "shaded" by the overhanging material.

This embodiment which is shown with reference to FIGS. 11-16 thus concerns the insulation of groups of needles.

Thereby, in a first step there is provided an insulating trench which delimits a defined area, large enough to house a plurality of needles, subsequently made. The same procedural steps described previously herein are used also in this embodiment and schematically illustrated in FIG. 11-16.

Figure 11:
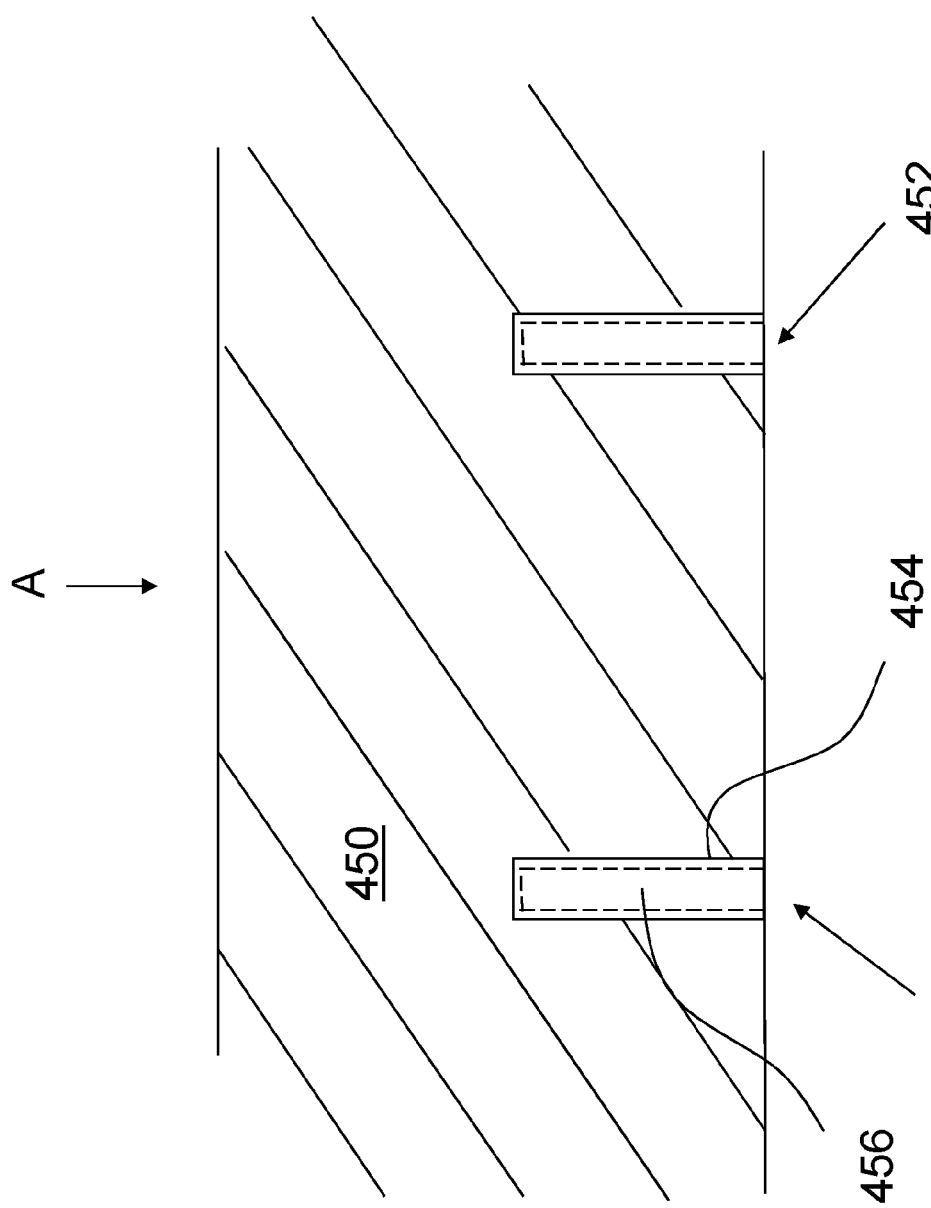
FIG. 11 shows a first stage in an alternative process for insulating groups of needles in cross-section.
Figure 12:
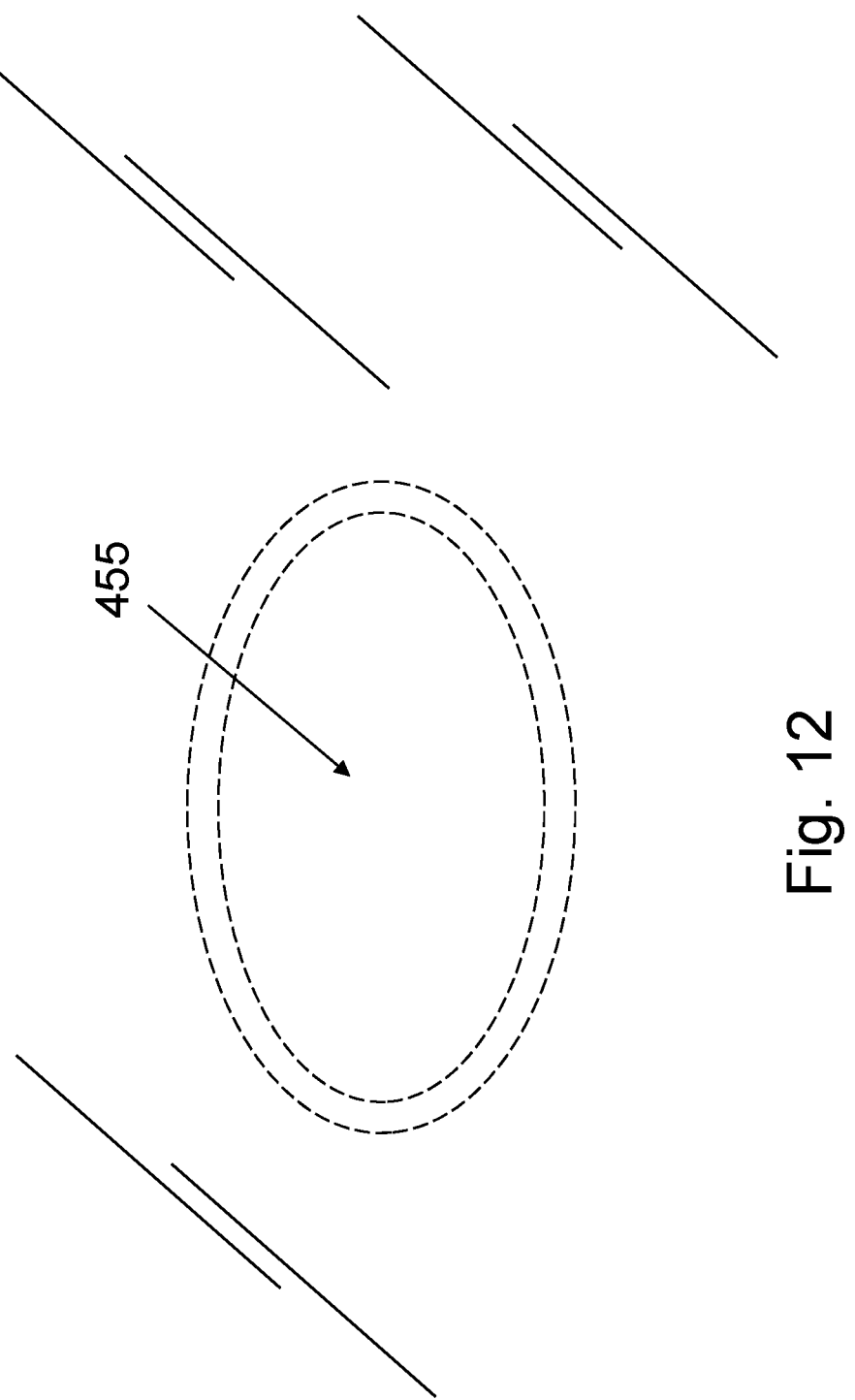
FIG. 12 illustrates the first stage in a top view.

Thus, first a trench is etched in a substrate wafer, oxidized so as to fill entirely with oxide or optionally filled with some other filler material, schematically shown in FIG. 11, wherein the wafer is designated 450, the trench indicated at 452, the oxide layer with 454 and the filler material with 456 (shown in broken lines to indicate the optional character). The same reference numerals will be used in the following figures. The intermediate state shown in FIG. 11 in cross-section is shown in FIG. 12 in a top view seen in the direction of the arrow A in FIG. 12. Thus, here the trench (indicated in broken lines since it is not visible) forms an ellipse delimiting an area 455 of the wafer, although any other shape is equally possible.

Figure 13:
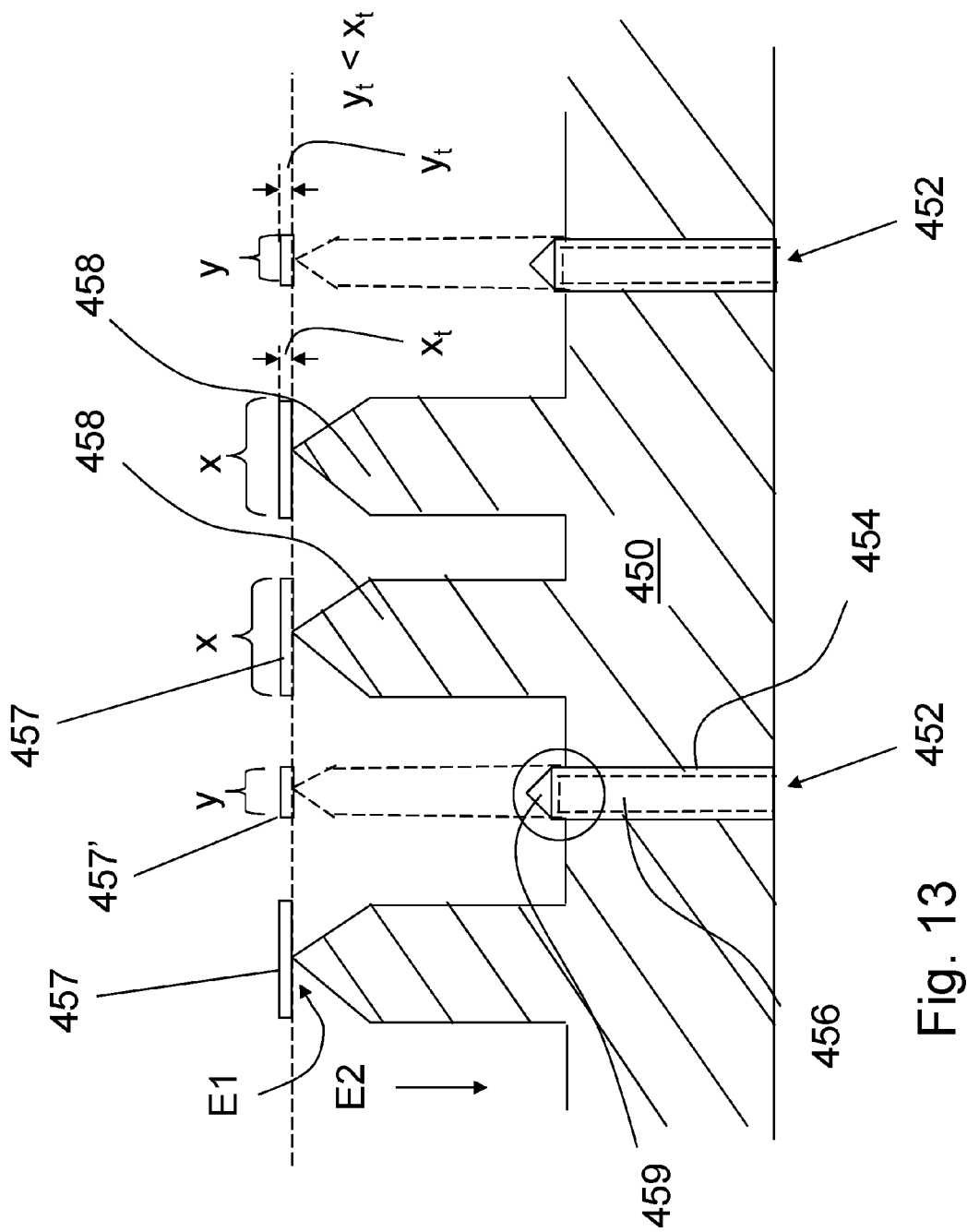
FIG. 13 shows a second stage in the alternative process for insulating groups of needles in cross-section showing needles and an insulating ridge.
Figure 14:
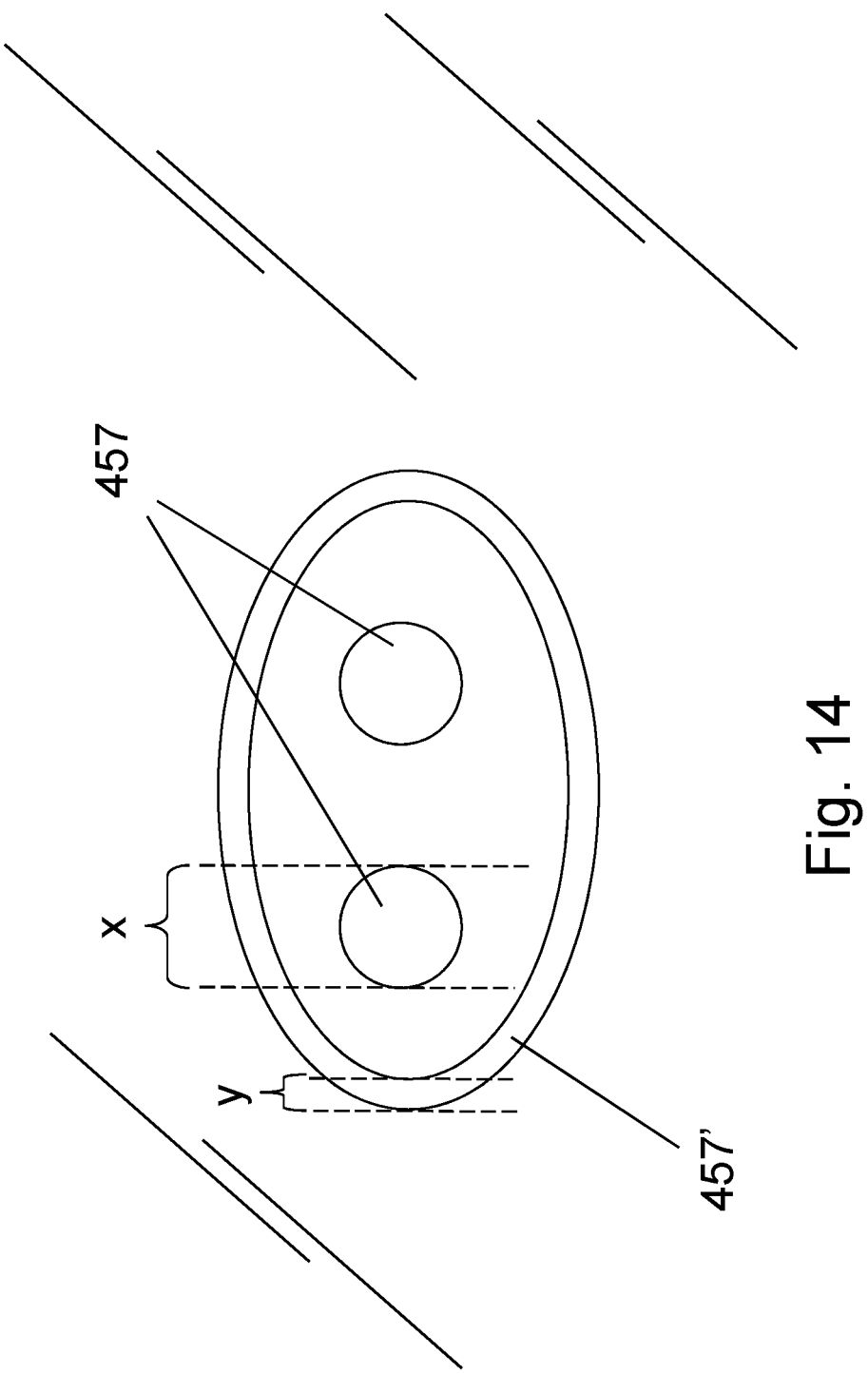
FIG. 14 is a top view of the second stage.

Next, by patterning (to provide masks 457, 457') and etching (arrows E1 and E2) procedures described herein previously with reference to FIGS. 13-14, needles 458 are made as shown in FIG. 13. A first isotropic etch E1 is made to underetch the masks 457 to provide the tips of the needles, and then an anisotropic etch is preformed to provide the pillars. As can be seen in FIG. 13 the needles 458 are made from wafer material in the area defined by the circumference of the trench. The width of the needles is designated x. FIG. 14 shows the wafer with masks 457', 457 in a top view.

Furthermore, in FIG. 13 it is shown that by appropriate patterning and masking of the substrate 450, i.e. by covering an area corresponding to the entire trench with a mask 457', it is possible to arrive at the encircled structure shown in FIG. 13.

This is possible by appropriate selection of the values the diameter (x) of the actual mask 457 for the needles 458 and the width (y) of the mask 457' covering the trench.

The requirement is that x>y.

Since y<x the first etch E1 will etch away all material under the mask 457' before the tip of the needles 458 under the mask 457 is finished. When the second etch E2 is initiated it will remove material anisotropically such that the height of the structure originally defined by mask 457' will be reduced. Thus, by appropriate selection of x and y, one can tailor the process such that between the needle groups there will be a smaller structure the cross-section of which will degenerate into a triangle, optionally having a short vertical base portion formed by the oxide in the trench that is coming to be exposed, as shown. The structure obtained is of course rather a ridge 459 with a triangular cross-section, running along the trench and covering it. This is more clearly shown in FIG. 15(a) which is a schematic perspective view of the structure from FIG. 13.

In an alternative embodiment the mask x for the needles 458 is made thicker than the mask y for the ridge structure 459. Thus, when the needles have been say half finished the mask 457' for the ridge 459 will have disappeared, while the needle mask 457 will still protect the needle 458.

The structure as shown in FIG. 15(*a*) is now subjected to a wet HF etch which selectively removes oxide isotropically which means that it will eat away material in the region between the ridge 459 and the substrate surface 450'. Thereby, there will be an undercut portion 461 under the ridge 459, which will "shade" the area below, as can be seen in FIG. 15(*b*).

When the underetch has been made and the undercut portion 461 is created the wafer is metallized by some suitable method (e.g. sputtering). This provides a metal coating 462, as shown in FIG. 16, but because of the "shading" effect at the undercut portion 461 there will be a disruption in the coating effectively isolating the needles electrically from the surrounding wafer.

By carefully selecting the metal with which the needles are coated, it is also possible to avoid occurrence of thermo EMKs etc. Thus, the metal for the coating has to be selected such that the thermo EMK is eliminated or at least substantially reduced. The preferred choice is to select the coating to be identical to the substrate on which a measurement is to be made. For measurements in or on a human body AgCl is preferred.

The invention claimed is:

1. A method of providing a metal coating on a substrate, and electrically insulating sections/parts of the metal coated substrate, the steps comprising:
   providing a substrate having a first side and an opposite second side and a thickness therebetween;
   providing an insulating material in the substrate, said insulating material extending through the thickness of the substrate and protruding above one of the sides of the substrate, and forming an enclosed section/portion of the substrate by
   i) etching a trench in the substrate from the first side of the substrate, the trench extending almost through the substrate and forming a closed loop in order to enclose a piece of the substrate;
   ii) filling the trench with an insulating material, and
   iii) thinning down the substrate from the second side from which the trench was made, whereby the thinning is performed to such an extent, and selectively, that only the substrate is removed, and deep enough that the insulating material becomes exposed, and protrudes slightly from the second side of the substrate;
   providing a protective structure that covers the protruding insulating material;
   selectively etching away part of an oxide of the protruding insulating material thereby excavating insulating material from underneath the protective structure and providing an under-etch under a protective layer on both sides of the protruding insulating material; and
   depositing metal/conductive material to provide a metal coating over the second side of the substrate, whereby the under-etch will provide a disruption in the deposited metal coating, thereby electrically insulating the enclosed section/portion of the substrate from the other sections/parts of the metal coated substrate.

2. The method according to claim 1, wherein the under-etch is achieved by applying a wet isotropic HF etch or a dry isotropic etch.

3. The method according to claim 1, wherein the substrate is made of silicon.

4. The method according to claim 1, wherein the metal/conductive material is silver-chloride (AgCl).

5. A method of making devices for electrical measurements, each device comprising a plurality of micro-electrodes in the form of micro-needles protruding vertically from a substrate, the method comprising the steps of:
   providing a substrate having a first side and an opposite second side and a thickness therebetween;
   making trenches in the first side of the substrate, wherein each of the trenches have a thickness that is smaller than the thickness of the substrate and defines a respective area on the substrate, wherein the respective area is encircled by the respective trench in a closed loop;
   providing an insulating material in each of the trenches,
   making micro-needles from the second side of the substrate by a masking and etching process, wherein each of the micro-needles are located on an entire surface of the respective area encircled by the trench, wherein the step of etching further exposes the insulating material;
   performing a selective etch to remove part of the exposed insulating material to create an undercut below a base of each of the micro-needles; and
   subjecting the substrate and the micro-needles to a process for depositing a conductive/metal material whereby a region of the respective undercut will not be coated.

6. The method according to claim 5, wherein the etching and masking to make the micro-needles comprises:
   oxidizing the substrate;
   patterning the oxide on the second side of the substrate to define the micro-needles to be made;
   subjecting the second side to an oxide etch to remove oxide to provide a mask;
   performing an isotropic etch under the mask to create micro-needle tips;
   performing an anisotropic etch to create vertical micro-needle pillars.

7. The method according to claim 6, wherein the anisotropic etching is the Bosch process.

8. A micro-needle device, comprising:
   a semiconductor substrate having at least one micro-needle extending from a surface of the substrate,
   the micro-needle being provided on a portion of the substrate surrounded by a trench with an insulating material therein,
   the insulating material extending above the surface of the substrate,
   wherein there is an undercut portion at a base of the micro-needle,
   wherein the micro-needle is centered on the trench such that the circumference of the base of the micro-needle contacts the insulating material in the trench, whereby the undercut portion exposes the insulating material in the trench, and
   a metallization covering that covers at least part of the micro-needle and the substrate except at the undercut portion where there is a disruption in the metallization.

9. A micro-needle device, comprising:
   a semiconductor substrate having at least one micro-needle extending from a surface of the substrate,
   the micro-needle being provided on a portion of the substrate surrounded by a trench with an insulating material therein,
   the insulating material extending above the surface of the substrate,
   a ridge, wherein a base of the ridge contacts the extending insulating material; and wherein there is an undercut portion at the base of the ridge, whereby the undercut portion exposes the insulating material in the trench, and a metallization covering that covers at least part of the micro-needle and the substrate except at the undercut portion where there is a disruption in the metallization.

10. A micro-needle device comprising:

a semiconductor substrate with a first surface having at least one micro-needle extending from the surface, the substrate further including a trench with an insulating material therein, the insulating material extending above the surface of the substrate, wherein the at least one micro-needle is provided on a portion of the substrate surrounded by the trench, such that the circumference of the at least one micro-needle contacts the insulating material in the trench, the insulating material includes an undercut portion located adjacent to the at least one micro-needle; and a metallization covering that covers at least part of the at least one micro-needle and the substrate except at the undercut portion where there is a disruption in the metallization.

\* \* \* \* \*